(12) United States Patent
Hesse et al.

(10) Patent No.: US 7,008,632 B2
(45) Date of Patent: Mar. 7, 2006

(54) COMBINATION OF BIOLOGICAL AND CHEMICAL AGENTS TO COMBAT RODENTS

(75) Inventors: Gerhard Hesse, Wermelskirchen (DE); Thomas Böcker, Leichlingen (DE); Stefan Endepols, Köln (DE); Thomas Jäkel, Stuttgart (DE); Sermasakdi Hongnark, Bangkok (TH)

(73) Assignee: Bayer Aktiengesellschaft, Leverkusen (DE)

( * ) Notice: Subject to any disclaimer, the term of this patent is extended or adjusted under 35 U.S.C. 154(b) by 114 days.

(21) Appl. No.: 10/181,341

(22) PCT Filed: Jan. 5, 2001

(86) PCT No.: PCT/EP01/00091

§ 371 (c)(1), (2), (4) Date: Sep. 23, 2002

(87) PCT Pub. No.: WO01/52654

PCT Pub. Date: Jul. 26, 2001

(65) Prior Publication Data

US 2004/0028713 A1 Feb. 12, 2004

(30) Foreign Application Priority Data

Jan. 18, 2000 (DE) .............................. 100 01 801

(51) Int. Cl.
*A01N 25/32* (2006.01)
(52) U.S. Cl. ............... 424/406; 424/84; 424/271.1; 424/405; 514/457
(58) Field of Classification Search ........ 424/405–406, 424/408, 409–410, 84, 271.7; 514/457
See application file for complete search history.

(56) References Cited

U.S. PATENT DOCUMENTS

| | | | | |
|---|---|---|---|---|
| 2,957,804 A | * | 10/1960 | Shuyler | 424/10.3 |
| 3,882,104 A | | 5/1975 | Grisar et al. | 424/240 CA |
| 4,011,332 A | | 3/1977 | Schoetensack et al. | 260/273 |
| 5,132,321 A | | 7/1992 | Corey | 514/457 |

FOREIGN PATENT DOCUMENTS

| | | |
|---|---|---|
| CH | 481 580 | 1/1970 |
| GB | 1 371 135 | 10/1974 |
| JP | 480 23 942 | 3/1973 |
| WO | 99/45578 | 9/1999 |
| WO | 9945778 | 9/1999 |

OTHER PUBLICATIONS

International Jouranl for Parasitology, vol. 4, (month unavailable) 1974, pp. 447-449, C. M. Rzepczyk, "Evidence of a Rat-Snake Life Cycle for *Sarcocystis*".

Database Biosis Online! Biosciences Information Service, Philadelphia, PA, US; 1996 Jaekel Thomas et al: "Sarcocystis singaporensis: Studies on Host specificity, pathogenicity, and potential use as a biocontrol agent of wild rats." Database accession No. PREV199698822203 XP002172036 & Journal of Parasitology, Bd. 82, Nr. 2, 1996, Seiten 280-287.

Z. Parasiten, 47, (month unavailable) 1975, pp. 169-185, V. Zaman and Frederick C. Colley, Light and Electron Microscopic Observations of the Life Cycle of *Sarcocystis orientalis* ap. n. in the Rat (*Rattus norvegicus*) and the Malaysian Reticulated Python (*Python reticulates*).

Acta Physiol. Pharmacol. Neerl. 14, (month unavailable) 1967, pp. 423-433, P.M.L. Tammes, F.E. Loosies and R. Wijnen, "Time-Response Experiments With Anticoagulants on Rats".

Z. Parasitenkd, 62, (month unavailable) 1980, pp. 15-30, Helga Brehm und Werner Frank; "Der Entwicklungskreislauf von *Sarcocystis singaporensis* Zaman und Colley, 1976 im End- und Zwischenwirt".

Beiheft Z. Angew. Zool., 155, (month unavailable) 1974, pp. 155-159, L. Papocsi, "Die Praktische Darchführung der totalen Entrattung von Budapest 1. Das Entrattungssytem von Baboina".

(Aug. 1999) Jaekel T et al: "Biological control of rodents using Sarcocystis singaporensis." Database accession No. PREV19900520606 XP002172037 Zusammenfassung & International Journal For Parasitology, Bd. 29, Nr. 8, Aug. 1999, Seiten 1321-1330, ISSN: 0020-7519.

Burgstaller H et al: "Biological control of field rats in Egypt with special consideration of native predators." Database accession No. PREV199497072443 XP002172038 Zusammenfassung & Journal of Plant Protection In The Tropics, Bd. 9, Nr. 1, 1992, Seiten IV, 25-41, ISSN:0127-6883.

* cited by examiner

*Primary Examiner*—Neil S. Levy
(74) *Attorney, Agent, or Firm*—Richard E. L. Henderson; Raymond J. Harmuth

(57) ABSTRACT

The present invention relates to compositions comprising sporocysts of at least one parasitic single-cell organism and at least one anticoagulant, and to their use for controlling harmful rodents.

4 Claims, No Drawings

COMBINATION OF BIOLOGICAL AND CHEMICAL AGENTS TO COMBAT RODENTS

The present invention relates to compositions comprising pathogenic single-cell organisms and anticoagulants, and to their use for controlling rodents.

It is known that indandione derivatives and 4-hydroxycoumarins are antagonists of vitamin K and lower the prothrombin level in the blood. This reduces the coagulability of the blood. Moreover, these compounds increase the permeability of the microcapillaries. In particular, rodents are highly sensitive to these substances. Accordingly, these derivatives are used as rodenticidal active compounds (cf., for example, DE-OS (German Offenlegungschrift) 25 06 769, JP-A 48 023 942, CH-OS (Swiss Offenlegungschrift) 481 580, Tammes P M L et al. 1967 Acta Physiol. Pharmacol. Neer. 14, 423–433, Paposci L 1974 Beihefte Z. Angew. Zool., 155, DE 2 506 769).

The acute toxicity of the active compounds of this group which are currently marketed is from 0.2 mg/kg to 30 mg/kg (LD50 rat). For coumatetralyl, for example, the LD50 is about 16.5 mg/kg. The acute LD50 for anticoagulants of the second generation is from 0.2 mg/kg (brodifacoum) to 2.0 mg/kg (bromadiolone). In resistant rats, the respective LD50 can be higher by a factor of 10–100. (All data refer to the acute oral LD50 for *Rattus norvegicus*).

It is also known that protozoa from the group of the Sarcosporidia (phylum Protozoa, class Sporozoa, sub-class Coccidia, order Eucoccidiida, sub-order Eimeriina) are pathogenic for rodents (genera *Rattus, Bandicota, Arvicanthis, Nosokia, Mus*) and, at a high enough dosage, lead to the death of the animals (Rzepczyk 1974, Intern. J. Parasitol. 4, 447449; Brehm, Frank 1980, Z. Parasitenkd. 62, 15–30). A parasite of this group which is particularly pathogenic for a plurality of rat species is *Sarcocystis singaporensis* (Zamann et al. 1975, Z. Parasitenkd. 47, 169–185).

Final hosts of the parasites are carnivores or omnivores; in the case of *S. Singaporensis*, the final hosts are snakes, for example the reticulated python. In the intestine of the final host, the parasite forms sporocysts. These resting stages are excreted with the faeces. If an intermediate host, in the case of *S. singaporensis* for example a rat, is infected orally with these sporocysts, sporozoites hatch in the intestine of the rat and permeate the intestinal wall. Via the blood circulation, these stages migrate into other organs, where they can multiply by division (schizogony).

Two schizogonies were demonstrated, the first around the sixth day p.i. and the second around day 14–16 p.i. The schizonts occur in particularly large numbers in the lung, where they multiply in the endothelial cells.

If, owing to a severe infection, there is a mass multiplication of the merozoites in the lung, the rat falls ill during the second schizogony of the parasite around day 16 p.i. and in most cases dies within a few hours.

It is possible to feed the sporocysts of these sarcosporidia to rodents, so that the latter die as a consequence of the infection. This principle can be utilized for controlling rodents (Wood 1985, J. Plant Protect. Trop. 2, 67–69). Rats have already been controlled successfully using *Sarcocystis singaporensis* (Jäkel et al. 1996, J. Parasitol. 82, 280–287).

Infections of *Rattus rattus* and *norvegicus* with more than 20 000 sporocysts are usually lethal. Up to 14 days p.i., the animals show no symptoms. Then, they very rapidly become weak and die as a consequence of the infection, around day 16 p.i.

Even after 14 days p.i., sublethally infected rats show hardly any symptoms of being ill and survive the infection without loss of vitality. Even a few days after the infection, these animals have built up immunity to the pathogen. These animals are thus insensitive to any further control with a *Sarcocystis singaporensis* preparation.

Surprisingly, it has now been found that sublethally infected animals can be killed by a single administration of an anticoagulant.

Here, it is particularly remarkable that an anticoagulant dosage considerably below the LD50 for normally sensitive animals is sufficient for this purpose (see example). Less than half of the LD50 (acute oral) is required to achieve 100 percent mortality. In the case of coumatetralyl, for example, even 6 mg/kg are sufficient for *Rattus norvegicus*.

It should be particularly emphasized here that even a single low dosage of anticoagulants which are usually effective only after having been ingested more than once is sufficient to achieve 100% mortality.

Surprisingly, the effect of an infection with *Sarcocystis* sporocysts is enhanced synergistically by sublethal quantities of an anticoagulant. This provides a novel and unexpected possibility for considerably more effective control of harmful rodents.

Suitable pathogenic organisms are, in principle, all protozoa from the class Sporozoa. Particularly suitable are species from the sub-class Coccidia. Very particularly suitable are representatives of the sub-order Eimeriina. By way of example, but not by way of limitation, the species of the genus *Sarcocystis*, such as *S. singaporensis*, may be mentioned.

Suitable synergists for an infection with Sarcosporidia in the system according to the invention are, in principle, all anticoagulant rodenticidal active compounds. In this context, reference may be made, in particular, to the anticoagulant substances, such as the 4-hydroxycoumarin derivatives (1-phenyl-2-acetyl)-3-ethyl-4-hydroxycoumarin ("warfarin"), 3-(α-acetonyl-4-chlorobenzyl)-4-hydroxycoumarin ("coumachlor"), 3-(4'-hydroxy-3'-coumarinyl)-3-phenyl-1-(4'-bromo-4'-biphenyl)-propan-1-ol ("bromadiolone"), 3-(3'-paradiphenylyl-1',2',3',4'-tetrahydro-1'-naphthyl)-4-hydroxycoumarin ("difenacoum"), brodifacoum, flocoumafen and 3-(1',2',3',4'-tetrahydro-1'-naphthyl)-4 -hydroxycoumarin ("coumatetralyl"), the indandione derivatives, such as 1,1-diphenyl-2-acetyl-indan-1,3-dione ("diphacinone") and (1'-p-chlorophenyl-1'-phenyl)-2-acetyl-indan-1,3-dione ("chlorodiphacinone"), and the hydroxy-4-benzothiopyranones, for example difethialone.

Further anticoagulants suitable for preparing the compositions according to the invention which may be mentioned are the following 2-azacycloalkylmethyl-substituted benzhydryl ketones and carbinols:

1-phenyl-3-(2-piperidyl)-1-(p-tolyl)-2-propanone, 3,3-diphenyl-1-(2-pyrrolidinyl)-2-pentanone, 1,1-diphenyl-3-[2-(hexahydro-1H-azepinyl)]-2-propanone, 1-(4-fluorophenyl) -1-phenyl-3-(2-piperidyl)-2-propanone, 1-(4-methylthiophenyl)-1-phenyl-3-(5,5-dimethyl-2-pyrrolidinyl)-2-propanone, 1-(p-cumenyl)-1-phenyl-3-(4-tert-butyl-2-piperidinyl)-2-propanone, 3,3-diphenyl-1-[2-(hexahydro-1H-azepinyl)]-2-butanone, 3-(2,4-dichlorophenyl)-3-phenyl-1-(2-piperidyl)-2-heptanone, 1,1-diphenyl-3-(5-methyl-2-pyrrolidinyl)-2-propanone, 3,3-diphenyl-1-(2-piperidyl)-2-butanone, α-(α-methyl-α-phenylbenzyl)-2-piperidineethanol, α-(α-ethyl-α-phenylbenzyl)-2-pyrrolidineethanol, (2,5-dimethyl-α-phenylbenzyl)-2-piperidineethanol and α-(diphenylmethyl)-2-(hexahydro-1H-azepine)ethanol and salts thereof, described in DT-OS (German Offenlegungschrift) 2417783, and also 4'-(fluorophenyl)-2-(2-pyrrolidinyl)-acetophenone, 4'-phenyl-2-(5,5-dimethyl-2-pyrrolidinyl)-acetophenone, 4'-[p-(trifluoromethyl)-phenyl]-2-(2-piperidyl)-acetophenone, 4'-(p-butoxyphenyl)-2-(4-tert-butyl-2-piperidyl)-acetophenone, 2'-phenoxy-2-(2-piperidyl)-acetophenone, 4'-(p-fluorophenoxy)-2-(5,5-dimethyl-2-pyrrolidinyl)-acetophenone, 4'-(p-chlorophenoxy)-2-(2-piperidyl)-acetophenone, 4'-[m-(trifluoromethyl)-phenoxy]-2-(2-piperidyl)-acetophenone, 4'-(p-butoxyphenoxy)-2-(2-pyrrolidinyl)-acetophenone, 2-(2-piperidyl)4'-(trans-p-tolylvinylene)-acetophenone, 2-(2-hexahydro-1H-azepinyl)4'-(trans-styryl)-acetophenone, 4'-(m-methoxyphenylvinylene)-2-(2-pyrrolidinyl)-acetophenone, 2-(2-piperidyl)4'-[(p-methylthio)-phenylvinylene]-acetophenone, 4'-(3-phenoxypropoxy)-2-(2-piperidyl)-acetophenone, 4'-(4-phenylbutyl)-2-(2-piperidyl)-acetophenone, 4'-(α,α-dimethylbenzyl)-2-(piperidyl)-acetophenone, 4'-phenethyl-2-(3,5-diethyl-2-piperidyl)-acetophenone, 4'-phenyl-2-(2-pyrrolidinyl)-acetophenone, α-[2(2-phenyl-ethoxy)-phenyl]-2-piperidineethanol, α-(p-phenoxyphenyl)-2-pyrrolidineethanol, α-[4-(4-bromophenoxy)-phenyl]-6-methyl-2-piperidineethanol, α-(p-phenethyl)-phenyl-2-pyrrolidineethanol, α-p-bisphenyl-2-(hexahydro-1H-azepine)-ethanol, α-[3-(4-phenoxybutoxy)-phenyl]-2-piperidineethanol and α-(4-benzyl)-phenyl-2-piperidineethanol and salts thereof, described in DT-OS (German Offenlegungschrift) 2 418 480.

Especially, but not by way of restriction, the active compounds of the first generation, chlorophacinone, warfarin and coumatetralyl, and those of the early second generation, bromadiolone and difenacoum, may be mentioned.

The composition according to the invention can be incorporated into all recipes customarily used for preparing food baits for rodents, for example in baits based on cereals, in pastes, gels and blocks of wax and in extrudated mixtures of cereals and formulation auxiliaries. It is furthermore possible to offer the pathogens in drink baits based on water. The baits according to the invention are used like customary baits for controlling harmful rodents. They can be placed in buildings and outdoors, depending on the target species and the bait site density, at from 5 g to 500 g per bait site. They can also be placed into the entrance of the burrows of the rodents to be controlled.

The dosage of the pathogens in the bait should be from 500 to 200 000 sporocysts per gram of bait. Preference is given to concentrations of from 2000 to 50 000 sporocysts per gram, and 10 000 sporocysts per gram are particularly preferred. Higher dosages are also possible, but usually not necessary. It is possible to use both sporocysts of only one pathogen species and mixtures of sporocysts of different pathogens.

The concentration of the anticoagulant active compounds should be from about 10% to 150% of the concentrations which are customarily used and/or registered, for example as follows:

warfarin 30–600 ppm
coumatetralyl 30–400 ppm
bromadiolone 5–60 ppm
difenacoum 5–60 ppm
brodifacoum 3–50 ppm
flocoumafen 3–50 ppm
difethialone 3–50 ppm.

Preference is given to using the active compounds in the range from 10% to 25% of the concentrations which are customarily used and/or registered. It is possible here to employ an individual active compound or else a mixture of different suitable active compounds.

The parasite and anticoagulant active compound or active compound mixture can be offered simultaneously or at different times in separate baits. However, it is also possible to mix both in one bait and to control harmful rodents using this combination bait. The combination in one bait is a particularly useful solution.

For the purpose of the invention, rodents to be controlled or harmful rodents are rodents of the order Rodentia. Particular emphasis is given to the genera *Rattus, Mus, Bandicota, Nosokia* and *Microtus*. Very particular emphasis is given to the representatives of the genera *Rattus* and *Bandicota*, for example *R. rattus, R. norvegicus, B. bengalensis, B. indica.*

By using the system according to the invention, it is possible to restrict the quantity of anticoagulants and pathogenic organisms used. The concentration of the anticoagulants in the organisms is reduced, since only a low concentration of anticoagulant is required in the bait.

By using the system according to the invention, it is ensured, in particular, that even harmful rodents which are initially only infected sublethally are killed during the control measure. To repeat the infection of these animals would no longer be possible, since they would be immune after the first infection.

It is to be emphasized that the system according to the invention provides a useful instrument for resistance management. The probability of the development of resistance to the combination of different mechanisms of action is considerably lower than the probability of selection of a resistance to an individual principle of action.

The use of the system according to the invention ensures that the proportion of rats surviving the control measures is lower than if only one mechanism of action is used. In particular with respect to a control using *Sarcocystis*, it is to be emphasized that fewer of the animals immunized against *Sarcocystis* survive the control measures.

The present invention is based on the synergistic effect of two principles of action. This combination is a component of "Integrated Pest Management" with the aim of achieving a more effective control of harmful organisms whilst using lower quantities of active compounds, thus reducing the impact on the environment.

An experimental example is intended to illustrate the synergistic effect of the two principles of action.

EXAMPLE

Experiment Using Feral Adult Brown Rats (*Rattus norvegicus*)

Three groups of feral rats were treated with the same dosage of 1) sporocysts of *Sarcocystis singaporensis*, 2) the anticoagulant coumatetralyl and 3) the combination of sporocysts and coumatetralyl. The mortality was determined.

Empirically, the minimum sporocyst dosage for a lethal effect is 20 000 sporocysts per animal. The LD50 of coumatetralyl for non-resistant rats is 16.5 mg/kg (Racumin, Technische Information Bayer AG).

The rats were raised under standard conditions in the laboratory. During the experiment and the 2-week preparation, they were kept individually in cages made of Makrolon. Sporocyst suspension and coumatetralyl were administered by gavage, and during the administration the animals were anesthetized lightly using diethyl ether.

| Group 1 (S): | 10 000 sporocysts, in 0.5 ml of a suspension in polyethylene glycol 300 containing 20 000 sporocysts per ml. |
| --- | --- |
| Group 2 (C): | 6 mg of coumatetralyl per kg of body weight, by means of 0.06 ml of a 1% strength solution of the active compound in polyethylene glycol 300 |
| Group 3 (S + C): | 10 000 sporocysts + 6 mg of coumatetralyl/kg administered analogously to groups 1 and 2. |

| Mortality | $n_{lethal}/n$ | % |
| --- | --- | --- |
| Group (S) | 0/6 | 0 |
| Group (C) | 1/6 | 17* |
| Group (S + C) | 6/6 | 100 |

* No haemorrhages were found

The invention claimed is:

1. A synergistic composition for controlling organisms of the species *Rattus norvegicus*, said composition comprising:
one or more sporocysts of the single-cell parasite species *Sarcocystis singaporensis*, and one or more anticoagulant active compounds selected from the group consisting of chlorophacinone, warfarin, coumatetralyl, bromadiolone and difenacoum;
wherein an amount of the sporocyst and/or an amount of the coagulant active compound present in said composition are each respectively below a level that if administered to said organism individually would have a lethal effect on said organism.

2. The composition according to claim 1 wherein said *Rattus norvegicus* is administered by gavage in the range of about 10,000 sporocysts and 6 milligram of coumatetralyl per kilogram of body weight.

3. A composition for exterminating the species *Rattus norvegicus* comprising:
one or more sporocysts of the species *Sarcocystis singaporensis*; and
coumatetralyl,
wherein the amount of the sporocysts and/or of coumatetralyl in said composition are each respectively below a level that if administered to said species individually would have a lethal effect to said species.

4. The composition according to claim 1 wherein said anticoagulant active compound is coumatetralyl.

* * * * *